United States Patent
Moeller

(10) Patent No.: US 8,666,738 B2
(45) Date of Patent: Mar. 4, 2014

(54) BIOMETRIC-SENSOR ASSEMBLY, SUCH AS FOR ACOUSTIC REFLECTOMETRY OF THE VOCAL TRACT

(75) Inventor: Lothar Benedikt Moeller, Monmouth County, NJ (US)

(73) Assignee: Alcatel Lucent, Paris (FR)

( * ) Notice: Subject to any disclaimer, the term of this patent is extended or adjusted under 35 U.S.C. 154(b) by 310 days.

(21) Appl. No.: 13/114,298

(22) Filed: May 24, 2011

(65) Prior Publication Data
US 2012/0300961 A1  Nov. 29, 2012

(51) Int. Cl.
*G10L 15/00*  (2013.01)

(52) U.S. Cl.
USPC ........... 704/231; 704/233; 381/362; 381/390; 381/375; 381/376

(58) Field of Classification Search
USPC ........... 381/91, 122, 362, 390, 375, 376, 110; 704/200.1, 207, 223, 226, 235, 231, 704/233
See application file for complete search history.

(56) References Cited

U.S. PATENT DOCUMENTS

| | | | |
|---|---|---|---|
| 3,925,616 A * | 12/1975 | Sondhi | 704/201 |
| 4,821,326 A | 4/1989 | MacLeod | |
| 5,678,221 A | 10/1997 | Cahill | |
| 5,940,791 A | 8/1999 | Byrnes et al. | |
| 5,989,023 A * | 11/1999 | Summer et al. | 433/69 |
| 6,006,175 A | 12/1999 | Holzrichter | |
| 6,151,571 A | 11/2000 | Pertrushin | |
| 6,212,496 B1 | 4/2001 | Campbell et al. | |
| 6,223,157 B1 | 4/2001 | Fisher et al. | |
| 6,487,531 B1 | 11/2002 | Tosaya et al. | |
| 6,801,894 B2 | 10/2004 | Nakamura et al. | |
| 7,082,393 B2 * | 7/2006 | Lahr | 704/233 |
| RE39,336 E | 10/2006 | Pearson et al. | |
| 7,251,601 B2 | 7/2007 | Kagoshima et al. | |
| 8,074,656 B2 * | 12/2011 | Vaska et al. | 128/848 |
| 2002/0116177 A1 | 8/2002 | Bu et al. | |
| 2002/0194005 A1 | 12/2002 | Lahr | |
| 2003/0097254 A1 | 5/2003 | Holzrichter et al. | |
| 2003/0176934 A1 | 9/2003 | Gopalan et al. | |
| 2005/0071166 A1 * | 3/2005 | Comerford et al. | 704/272 |
| 2005/0244020 A1 | 11/2005 | Nakajima et al. | |
| 2005/0278167 A1 | 12/2005 | Burnett et al. | |

(Continued)

FOREIGN PATENT DOCUMENTS

WO  WO2007053562 A2  5/2007

OTHER PUBLICATIONS

PCT International Search Report dated Feb. 22, 2010, for PCT International Application No. PCT/US2009/064563.

(Continued)

*Primary Examiner* — Disler Paul
(74) *Attorney, Agent, or Firm* — Mendelsohn, Drucker & Dunleavy, P.C.

(57) ABSTRACT

A biometric-sensor assembly, e.g., for acoustic reflectometry of the vocal tract. In one embodiment, the sensor assembly includes a dental appliance for in-mouth mounting, an acoustic sensor attached to the dental appliance, and an optional headset. The dental appliance enables secure placement of the acoustic sensor in the mouth of the user, e.g., for tracking movements of the tongue and/or other internal articulators of the vocal tract. A boom arm of the headset can be used for holding an additional acoustic sensor and/or a miniature video camera, e.g., for tracking movements of the lips.

16 Claims, 5 Drawing Sheets

(56) References Cited

U.S. PATENT DOCUMENTS

| | | | |
|---|---|---|---|
| 2006/0200344 A1 | 9/2006 | Kosek et al. | |
| 2007/0101313 A1 | 5/2007 | Bodin et al. | |
| 2007/0276658 A1* | 11/2007 | Douglass | 704/205 |
| 2008/0010071 A1 | 1/2008 | Callahan et al. | |
| 2008/0154815 A1 | 6/2008 | Martinez | |
| 2008/0162119 A1 | 7/2008 | Lenhardt | |
| 2009/0120447 A1 | 5/2009 | Vaska et al. | |
| 2010/0007512 A1 | 1/2010 | Ghovanloo et al. | |
| 2010/0131268 A1 | 5/2010 | Moeller | |
| 2010/0217591 A1 | 8/2010 | Shpigel | |
| 2010/0310107 A1* | 12/2010 | Saila et al. | 381/363 |
| 2012/0259554 A1* | 10/2012 | Chen et al. | 702/19 |

OTHER PUBLICATIONS

Carrick Detweiler, et al., "Ultrasonic Speech Capture Board: Hardware Platform and Software Interface," May 14, 2008 Retrieved from the internet <URL:http://people.csail.mit.edu/carrick/papers/DetweilerV2008.pdf.> [Retrieved on Feb. 4, 2010] pp. 1-25.

Sharp, David Brian, "Acoustic Pulse Reflectometry for the Measurement of Musical Wind Instruments," PhD Thesis, Dept. of Physics and Astronomy, University of Edinburgh, 1996 (30 pages).

Notification of Transmittal of International Preliminary Report on Patentability; Mailed Jun. 2, 2011 for the corresponding PCT Application No. PCT/US2009/064563.

* cited by examiner

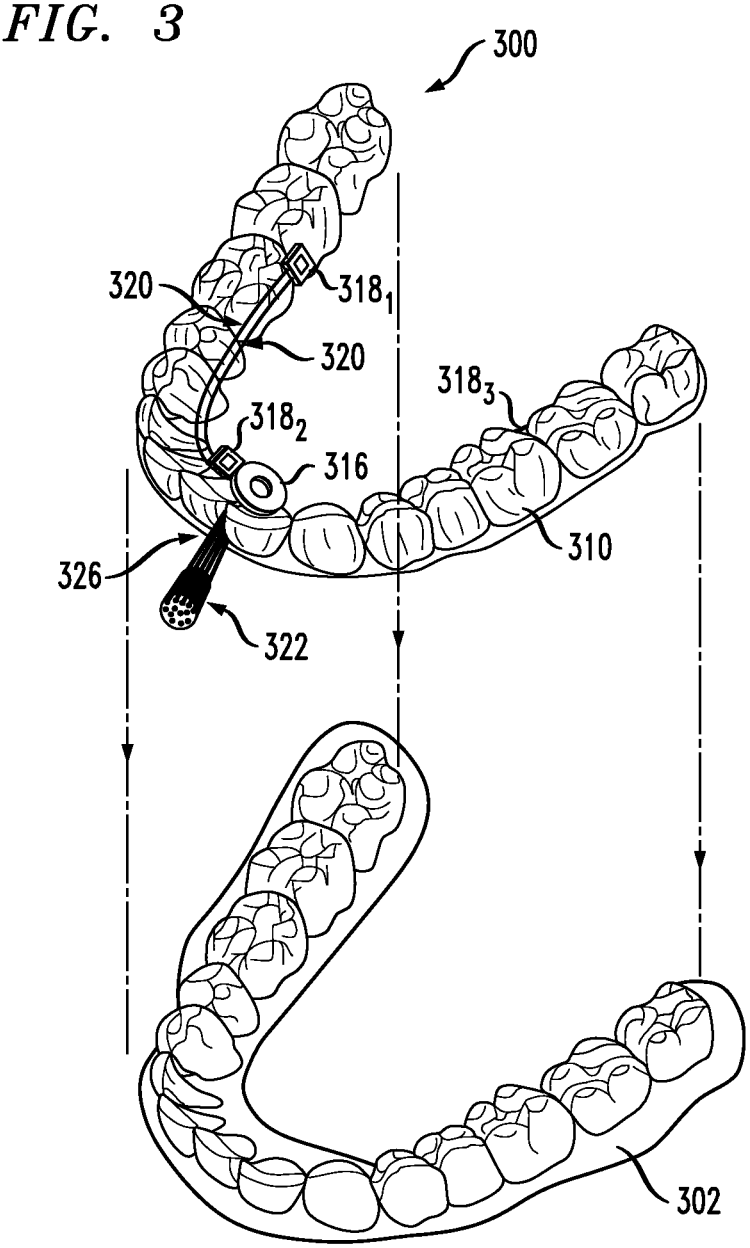

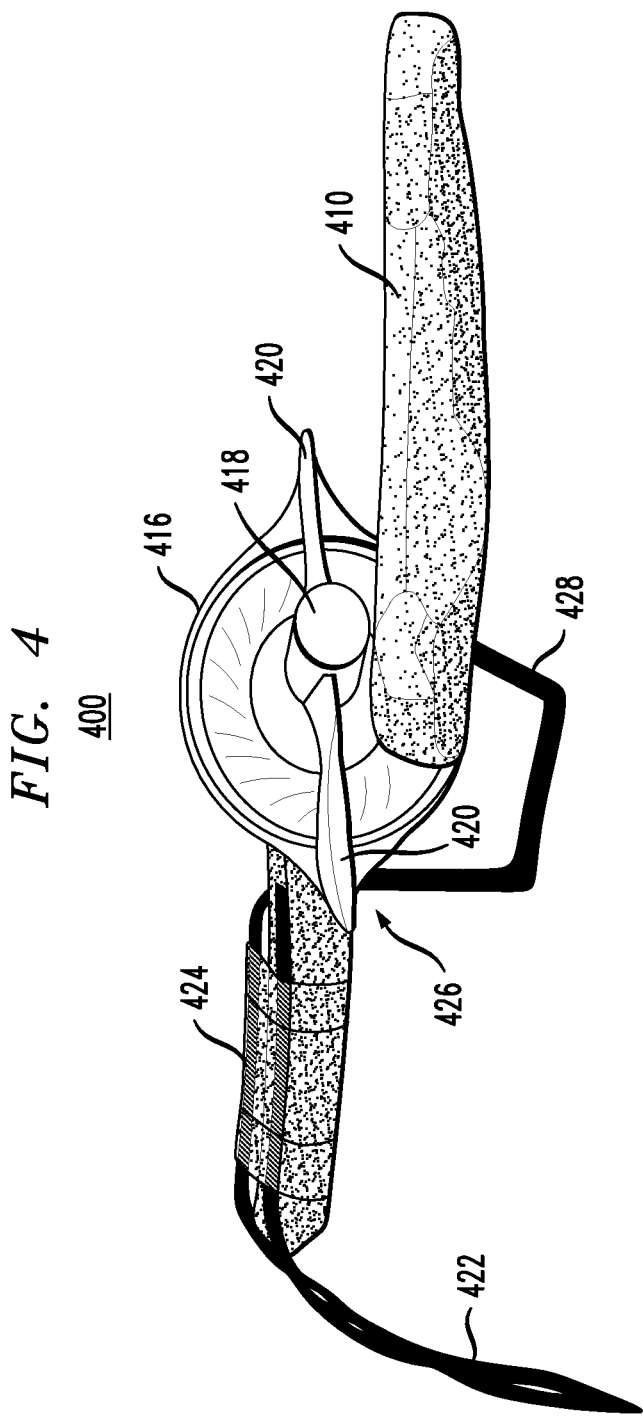

BIOMETRIC-SENSOR ASSEMBLY, SUCH AS FOR ACOUSTIC REFLECTOMETRY OF THE VOCAL TRACT

CROSS-REFERENCE TO RELATED APPLICATIONS

The subject matter of the present application is related to the subject matter of (1) U.S. Patent Application Publication No. 2010/0131268, (2) U.S. patent application Ser. No. 12/956,552, filed Nov. 30, 2010, and entitled "Voice-Estimation Based on Real-Time Probing of the Vocal Tract," and (3) U.S. patent application Ser. No. 13/076,652, filed Mar. 31, 2011, and entitled "Passband Reflectometer," all of which are incorporated herein by reference in their entirety.

The subject matter of this application is also related to the subject matter of U.S. Patent Application Publication No. 2012/0299826, which is incorporated herein by reference in its entirety.

BACKGROUND

1. Field of the Invention

The present invention relates to human-machine interfaces and, more specifically but not exclusively, to biometric sensors for probing the geometric shape of the vocal tract.

2. Description of the Related Art

This section introduces aspects that may help facilitate a better understanding of the invention(s). Accordingly, the statements of this section are to be read in this light and are not to be understood as admissions about what is in the prior art or what is not in the prior art.

The use of various biological signals produced by the human body for controlling machines and/or devices is currently being actively pursued. Body signals other than limb motion are useful, for example, for people with disabilities or when the hands/legs are being used for other functions. However, a human-machine interface suitable for these purposes and its various components, such as biometric sensors, are not yet sufficiently developed.

SUMMARY

Disclosed herein are various embodiments of a biometric-sensor assembly, e.g., for acoustic reflectometry of the vocal tract. In one embodiment, the sensor assembly includes a dental appliance for in-mouth mounting, an acoustic sensor attached to the dental appliance, and an optional headset. The dental appliance enables secure placement of the acoustic sensor in the mouth of the user, e.g., for tracking movements of the tongue and/or other internal articulators of the vocal tract. A boom arm of the headset can be used for holding an additional acoustic sensor and/or a miniature video camera, e.g., for tracking movements of the lips.

According to one embodiment, provided is an apparatus having a first acoustic speaker, a first set of one or more acoustic microphones, and a dental appliance. The first acoustic speaker and the first set of one or more acoustic microphones are attached to the dental appliance. When the dental appliance is placed into a user's mouth, the first acoustic speaker has a position that causes acoustic waves generated by the first acoustic speaker to enter the user's vocal tract, and the first set of one or more acoustic microphones has a position that causes acoustic waves reflected from the vocal tract to impinge onto at least one microphone of the first set.

According to another embodiment, provided is an apparatus having an acoustic speaker, a set of one or more acoustic microphones, and a headset having an earpiece and a boom arm that is movable with respect to the earpiece. The acoustic speaker is mounted on the boom arm. The set of one or more acoustic microphones is also mounted on the boom arm.

BRIEF DESCRIPTION OF THE DRAWINGS

Other aspects, features, and benefits of various embodiments of the invention will become more fully apparent, by way of example, from the following detailed description and the accompanying drawings, in which:

FIG. 3 shows a perspective three-dimensional view of a sensor assembly that can be used in the HM interface of the system shown in FIG. 1 according to another embodiment of the invention;

FIG. 4 shows a perspective three-dimensional view of a sensor assembly that can be used in the HM interface of the system shown in FIG. 1 according to yet another embodiment of the invention.

DETAILED DESCRIPTION

Figure 1:
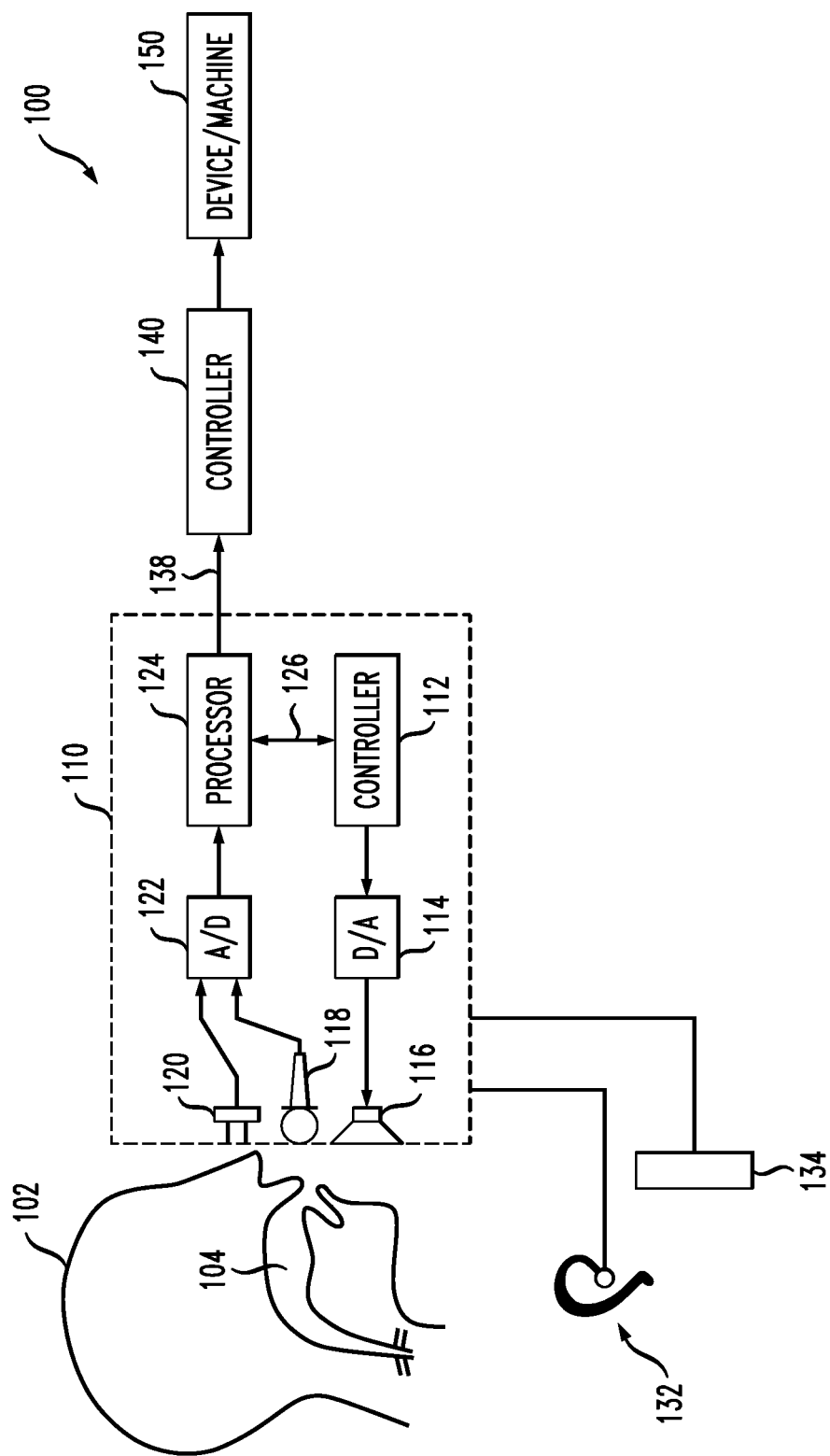
FIG. 1 shows a block diagram of a system having a human/machine (HM) interface according to one embodiment of the invention.

FIG. 1 shows a block diagram of an operator-controlled system 100 according to one embodiment of the invention. System 100 has a human/machine (HM) interface 110 that enables an operator (user) 102 to control the operation of a machine 150 using nonverbal signals produced by his/her vocal tract 104 and/or geometric degrees of freedom (DOFs) of the vocal tract. In various embodiments, machine 150 may be, without limitation, a mobility and/or prosthetic system for a disabled individual, a vehicle-control system, a multi-media system, a communication device, a machine that is being operated in a hostile environment (such as underwater, outer space, under high g-forces, or fire), and a weapon-control system.

Vocal tract 104 has multiple DOFs that enable intelligible speech and additional DOFs that are not used for speaking. For example, cartilage structures of the larynx can rotate and tilt variously to change the configuration of the vocal folds. When the vocal folds are open, breathing is permitted. The opening between the vocal folds is known as the glottis. When the vocal folds are closed, they form a barrier between the laryngopharynx and the trachea. When the air pressure below the closed vocal folds (i.e., sub-glottal pressure) is sufficiently high, the vocal folds are forced open. As the air begins to flow through the glottis, the sub-glottal pressure drops and both elastic and aerodynamic forces return the vocal folds into the closed state. After the vocal folds close, the sub-glottal pressure builds up again, thereby forcing the vocal folds to reopen and pass air through the glottis. Consequently, the sub-glottal pressure drops, thereby causing the vocal folds to close again. This periodic process (known as phonation) produces a sound corresponding to the configuration of the vocal folds and can continue for as along as the lungs can build up sufficient sub-glottal pressure. In general, the vocal folds will not oscillate if the pressure differential across the larynx is not sufficiently large.

The sound produced by the vocal folds is modified as it passes through the upper portion of vocal tract 104. More specifically, various chambers of vocal tract 104 act as acoustic filters and/or resonators that modify the sound produced by the vocal folds. The following principal chambers of vocal tract 104 are usually recognized: (i) the pharyngeal cavity located between the esophagus and the epiglottis; (ii) the oral cavity defined by the tongue, teeth, palate, velum, and uvula; (iii) the labial cavity located between the teeth and lips; and (iv) the nasal cavity. The shapes of these cavities can be changed by moving the various articulators of vocal tract 104, such as the velum, tongue, lips, jaws, etc. No sound is produced when a person simply moves the tongue, lips, and/or the lower jaw.

While operating system 100, operator 102 can activate the various parts of vocal tract 104 without producing a sound. For example, operator 102 can change the geometry of vocal tract 104 by consciously moving the tongue, lips, and/or jaws, without forcing an air stream through the larynx. Alternatively, operator 102 can change the geometry of vocal tract 104 by going through a mental act of "speaking to oneself," which causes the brain to send appropriate signals to the muscles that control the various articulators in the vocal tract without causing the vocal folds to oscillate. HM interface 110 characterizes the geometric shape of vocal tract 104 and/or its changes, e.g., as further described below, and then interprets the characterization results to generate a corresponding control signal (e.g., instruction or command) 138. In various embodiments, control signal 138 can be an analog signal or a digital signal. In one embodiment, operator 102 has control over the type of control signal 102 and can switch it between the analog and digital modes as appropriate or necessary. The latter feature may advantageously enable operator 102 to control machine 150 in a variety of fast-changing situations, for example, those experienced by a jet pilot under high-g forces.

Based on control signal 138, controller 140 configures machine 150 to perform a corresponding appropriate operation and/or function. In various embodiments, HM interface 110 can generate control signal 138 in a manner that enables (i) a continuous change of an operating parameter for machine 150 and/or (ii) a discrete change in the operating configuration or state of that machine. Representative examples of continuous changes include, without limitation, (a) changing the speed and/or direction of motion, (b) moving a robotic arm or tool, (c) moving a cursor across a display screen, (d) tuning a radio, and (e) adjusting the brightness and/or contrast of an image generated by night-vision goggles. Representative examples of discrete changes include, without limitation, (a) selecting an item or pressing an emulated button on a display screen, (b) starting or stopping an engine, (c) sending a silent message, and (d) firing a weapon.

In various embodiments, HM interface 110 can have different sensors configured to generate signals that characterize the geometric configuration of vocal tract 104. In the embodiment shown in FIG. 1, HM interface 110 includes a video camera 120 and an acoustic sensor comprising a speaker 116 and a microphone 118. In alternative embodiments, other suitable sensors and/or additional speakers and microphones (not explicitly shown in FIG. 1) may similarly be used. In a representative embodiment, HM interface 110 has at least one speaker and at least one microphone.

HM interface 110 has mechanical means (not explicitly shown in FIG. 1) for positioning and/or fixing the position of speaker 116, microphone 118, and camera 120 near the entrance to vocal tract 104, e.g., in or outside the mouth of operator 102 (also see FIGS. 2-5). Speaker 116 operates under the control of a controller 112 and is configured to emit short (e.g., shorter than about 1 ms) bursts of acoustic waves for probing the shape of vocal tract 104. In a representative configuration, a burst of acoustic waves generated by speaker 116 undergoes multiple reflections within the various cavities of vocal tract 104. The reflected acoustic waves are detected by microphone 118, and the resulting electrical signal is converted into digital form and applied to a digital signal processor 124 for processing and analyses. A digital-to-analog (D/A) converter 114 provides an interface between (i) controller 112, which operates in the digital domain, and (ii) speaker 116, which operates in the analog domain. An analog-to-digital (A/D) converter 122 provides an interface between (i) microphone 118, which operates in the analog domain, and (ii) processor 124, which operates in the digital domain. Controller 112 and processor 124 may use a digital-signal bus 126 to aid one another in the generation of drive signals for speaker 116 and the deconvolution of the response (echo) signals detected by microphone 118. Processor 124 uses the signals detected by microphone 118 together with the images captured by camera 120 to characterize the geometric configuration of vocal tract 104 and generate control signal 138 for controller 140.

As used herein, the term "acoustic" encompasses (i) sound waves from the human audio-frequency range (e.g., between about 15 Hz and about 20 kHz) and (ii) ultrasound waves (i.e., quasi-audio waves whose frequency is higher than the upper boundary of the human audio-frequency range, e.g., higher than about 20 kHz). Additional sensors for HM interface 110 can optionally be selected from a set consisting of an infrared sensor or imager, a millimeter-wave sensor, an electromyographic sensor, and an electromagnetic articulographic sensor. Further description of possible uses of these additional sensors can be found, e.g., in the above-cited U.S. Patent Application Publication No. 2010/0131268.

In one configuration, HM interface 110 characterizes the geometric shape of vocal tract 104 by repeatedly measuring its reflected impulse response. As used herein, the term "impulse response" refers to an echo signal produced by vocal tract 104 in response to a single, very short excitation impulse. Mathematically, an ideal excitation impulse that produces an ideal impulse response is described by the Dirac delta function for continuous-time systems or by the Kronecker delta for discrete-time systems. Since the excitation waveforms that are generated in practice are not ideal, the impulse response measured by HM interface 110 is an approximation of the ideal impulse response. In particular, various components of HM interface 110 may band-limit the frequency spectrum of the excitation pulse(s), limit the amplitude of the excitation pulses (e.g., to avoid undesired nonlinear effects), and/or band-limit the frequency spectrum of the detected reflected waves. The term "impulse response" should be construed to encompass both the transmitted impulse response and the reflected impulse response. In the context of HM interface 110, the measured impulse response is a reflected impulse response. However, known algorithms can be used to convert the measured reflected impulse response into a corresponding transmitted impulse response, with the latter being the impulse response that would have been measured at the distal end of vocal tract 104, e.g., the glottis.

When operator 102 changes the geometric shape of vocal tract 104, e.g., by moving the tongue, the impulse response of the vocal tract changes. In a representative configuration, HM interface 110 captures the corresponding series of impulse responses in real time, e.g., as described in the above-referenced U.S. patent application Ser. No. 13/076,652. Processor 124 can then use different signal-processing techniques to translate the captured impulse responses into control signal 138.

For example, in one embodiment, the signal processing implemented in processor 110 includes the determination, in some approximation, of the actual geometric shapes adopted by vocal tract 104, e.g., as described in the above-referenced U.S. patent application Ser. No. 12/956,552. The use of two or more microphones 118 configured for spatially resolved detection of impulse-responses enables HM interface 110 to recognize different asymmetrical shapes of vocal tract 104, with the asymmetry being ascertained with respect to the natural (left/right) plane of symmetry of the vocal tract. For example, acoustic signals detected by two or more microphones 118 placed at different laterally offset positions enable HM interface 110 to distinguish between a vocal-tract geometry in which the tongue is shifted toward the left cheek and the mirror-image geometry in which the tongue is equally shifted toward the right cheek.

In various embodiments, the signal processing implemented in processor 110 may be based on signal-feature selection and/or signal-feature quantification. A representative, non-exclusive list of signal features that can be selected for analysis includes (i) the delay between the excitation pulse and the corresponding impulse response, (ii) the amplitude and/or phase of a particular impulse response, (iii) the amplitude and/or phase of a differential impulse response derived from two impulse responses detected by two different microphones 118, and (iv) a frequency spectrum of an impulse response. In a representative embodiment, signal-feature quantification includes quantification of one or more parameters that describe the selected signal feature. A representative, non-exclusive list of possible signal-feature quantification steps includes (i) comparing a delay time with one or more reference values, (ii) comparing the intensity of a selected spectral component with one or more reference values, (iii) measuring the frequency of a characteristic frequency component of a signal, (iv) comparing a list of frequency components of a signal with a reference list, (v) comparing the intensities of two or more different frequency components with one another, (v) determining an amplitude and/or phase corresponding to a differential impulse response and comparing them to the corresponding reference values.

By configuring vocal tract 104 into certain geometric shapes, operator 102 can cause HM interface 110 to generate distinguishable signals that can be analyzed in terms of their features and mapped onto a set of commands/instructions. For example, while operating in a training mode, HM interface 110 can collect user-specific reference data and create a "map" of signal features according to which the detected impulse responses can be translated into the corresponding command(s)/instruction(s). The map is stored in the memory of HM interface 110 and invoked during normal operation of system 100. Based on the map, HM interface 110 interprets real-time vocal-tract reflectometry data and generates the corresponding appropriate control signal 138 for controller 140. Representative training procedures that can be used to collect user-specific reference data for HM interface 110 are disclosed, e.g., in the above-referenced U.S. Patent Application Publication No. 2010/0131268.

As already indicated above, the use of both analog and digital commands/instructions is possible. A representative example of generating an analog command is operator 102 moving the tip of the tongue from the upper-left wisdom tooth to the upper-right wisdom tooth while HM interface 110 is tracking the tongue position and translating the tongue displacement with respect to a reference position into an analog value. Controller 140 can then use this analog value to change some continuously variable operating parameter, such as the brightness of the image in night goggles 150 or the speed of vehicle 150. In one configuration, HM interface 110 enables operator 102 to use his/her tongue as a two-dimensional analog joystick, with an up/down tongue motion corresponding to one degree of freedom of the joystick and a left/right tongue motion corresponding to another degree of freedom.

The spatial resolution with which HM interface 110 can distinguish different geometric shapes of vocal tract 104 depends on the number of microphones 118 and their frequency characteristics, the characteristic frequencies and bandwidth of the excitation signal applied to the vocal tract by speaker 116, and the bandwidth of the recorded signal. Any possible command ambiguities due to the imprecise control of the geometric shape of vocal tract 104 by operator 102 and/or inadequate spatial resolution achieved by HM interface 110 can be resolved, e.g., by providing some form of feedback to the operator. In one embodiment, HM interface 110 is configured to provide an audio-feedback signal to operator 102 via an earpiece 132. Various visual forms of feedback are also contemplated, e.g., using a display screen 134. Based on the feedback signal(s), operator 102 can make a vocal-tract adjustment to enable HM interface 110 to unambiguously interpret the corresponding impulse-response features.

Figure 2A:
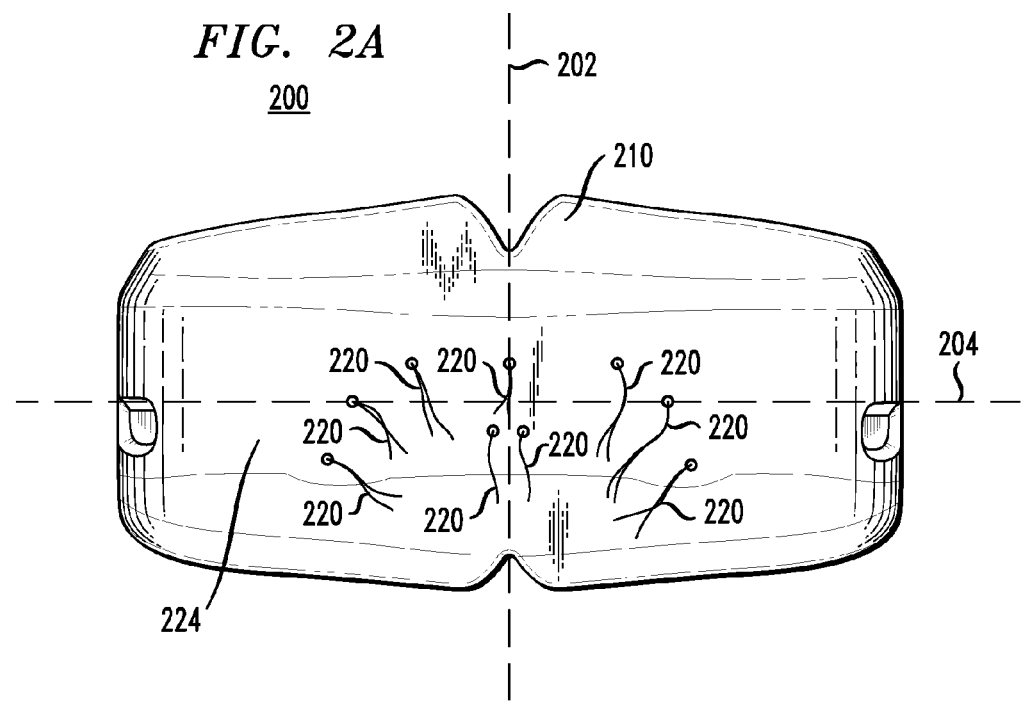
FIGS. 2A-2B show front and back views, respectively, of a sensor assembly that can be used in the HM interface of the system shown in FIG. 1 according to one embodiment of the invention.
Figure 2B:
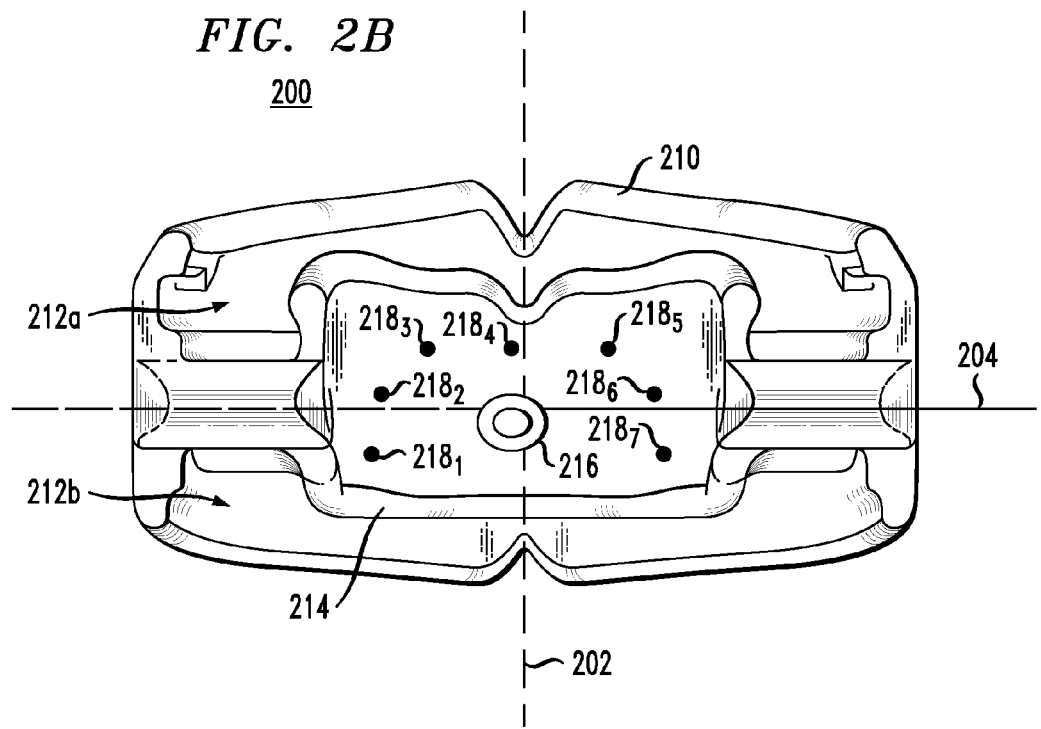

FIGS. 2A-2B show front and back views, respectively, of a sensor assembly 200 that can be used in HM interface 110 (FIG. 1) according to one embodiment of the invention. More specifically, when operator 102 wears sensor assembly 200, the front view shown in FIG. 2A corresponds to the frontal full-face view. The back view shown in FIG. 2B corresponds to a view from the interior of the operator's mouth.

Sensor assembly 200 comprises a mouthpiece 210 that can be similar in shape to a conventional mouthguard, e.g., a protective device for the mouth that covers the teeth and sometimes gums to prevent or reduce injury in contact sports or as part of certain dental procedures, such as tooth bleaching. Mouthpiece 210 is horseshoe-shaped and has an upper groove 212a and a lower groove 212b configured to accommodate the upper and lower arches of teeth, respectively. In various embodiments, mouthpiece 210 can be manufactured to have a relatively loosely accommodating shape that can fit the mouths of most operators or, alternatively, can be custom-molded to fit very closely to the teeth and gums of the particular operator 102. When worn by operator 102, mouthpiece 210 locks the operator's mandible and maxilla with respect to one another, which eliminates some degrees of freedom in vocal tract 104. The latter can be beneficial, e.g., for improving signal reproducibility and simplifying the concomitant signal processing implemented in processor 124.

In a representative embodiment, mouthpiece 210 has an approximately symmetric U shape characterized by two planes of approximate symmetry, both of which planes are orthogonal to the plane of FIG. 2. A first approximate-symmetry plane 202 is orthogonal to the plane of the U. A second approximate-symmetry plane 204 is parallel to the plane of the U.

Sensor assembly 200 further comprises a speaker 216 and seven microphones $218_1$-$218_7$, all of which are imbedded into a lingual wall 214 of mouthpiece 210 as indicated in FIG. 2B. A plurality of electrical lead wires 220 for electrically and respectively connecting speaker 216 and microphones $218_1$-$218_7$ to D/A converter 114 and A/D converter 122 (FIG. 1) protrude out from a labial wall 224 of mouthpiece 210 as indicated in FIG. 2A. In one embodiment, electrical lead wires 220 can be arranged into a cable (not explicitly shown in FIG. 2A). In an alternative embodiment, mouthpiece 210 incorporates a power source (e.g., a battery) and a short-range wireless transceiver (e.g., a Bluetooth transceiver), which eliminate the need for electrical lead wires 220. In this case, the base unit of HM interface 110 includes a corresponding short-range wireless transceiver configured to communicate with the wireless transceiver in mouthpiece 210.

In one embodiment, speaker 216 and microphone $218_4$ are positioned to approximately line up with approximate-symmetry plane 202. Speaker 216 and microphones $218_2$ and $218_6$ are positioned to approximately line up with approximate-symmetry plane 204. Microphones $218_1$-$218_3$ are positioned to the left of plane 202, and microphones $218_5$-$218_7$ are positioned to the right of plane 202. Microphones $218_3$-$218_5$ are positioned above plane 204, and microphones $218_1$ and $218_7$ are positioned below plane 204. The arrangement of microphones $218_1$-$218_7$ does not have to be symmetric, although certain benefits may accrue from a symmetric placement of the microphones. Taken together, microphones $218_1$-$218_7$ form a phase-arrayed acoustic detector that advantageously enables HM interface 110 to sense both lateral (left/right and up/down) and longitudinal (forward/backward) movements of the tongue. In an alternative embodiment, a different number of microphones 218 can similarly be used.

FIG. 3 shows a perspective three-dimensional view of a sensor assembly 300 that can be used in HM interface 110 (FIG. 1) according to another embodiment of the invention. Also shown in FIG. 3 is the lower arch 302 of teeth in the mouth of operator 102, to which sensor assembly 300 is form-fitted. The vertical dashed lines with arrows indicate how sensor assembly 300 is placed over arch 302.

Sensor assembly 300 comprises a U-shaped dental brace 310 configured for a relatively tight (e.g., form-fitting or snap-on) fit onto the teeth of arch 302. Sensor assembly 300 further comprises a speaker 316 and three MEMS microphones $318_1$-$318_3$ that are attached to brace 310 as indicated in FIG. 3. Note that the view of microphone $318_3$ is somewhat obscured by the corresponding side of brace 310. However, the way in which microphone $318_3$ is attached to brace 310 can be inferred from that of microphone $318_1$, which is similarly attached at the other (non-obscured) side of the brace. Electrical lead wires 320 run along the lingual surface of brace 310 from an entry point 326 to microphone $318_1$. Similar electrical lead wires (not clearly visible in FIG. 3) run from entry point 326 to speaker 316 and each of microphones $318_1$-$318_2$. At the labial side of brace 310, these electrical wires are assembled into a cable 322.

While the use of condenser microphones instead of MEMS microphones 318 is possible in alternative embodiments of sensor assembly 300, the use of MEMS microphones provides the benefit of a smaller size and lower power consumption. Each of microphones 318 has a housing that seals the microphone against saliva and other fluids to enable long-term wearing and even some food consumption with sensor assembly 300 remaining in the operator's mouth. Similar to sensor assembly 200, sensor assembly 300 can be modified for wireless operation. In an alternative embodiment, brace 310 can be configured to fit an upper arch of teeth and/or have a different number of microphones 318.

FIG. 4 shows a perspective three-dimensional view of a sensor assembly 400 that can be used in HM interface 110 (FIG. 1) according to yet another embodiment of the invention. Sensor assembly 400 differs from each of sensor assemblies 200 (FIG. 2) and 300 (FIG. 3) in that sensor assembly 400 has a speaker 416 and a microphone 418 that can optionally be positioned outside the mouth of operator 102, e.g., for tracking the position and/or movement of the operator's lips.

Sensor assembly 400 comprises a U-shaped dental brace 410 configured for a relatively tight fit to the upper or lower arch of teeth, such as arch 302 (FIG. 3), in the mouth of operator 102. In one embodiment, the whole sensor assembly 300 (including dental brace 310, speaker 316, microphones $318_1$-$318_3$, wires 320, and cable 322) can be used to implement dental brace 410.

Speaker 416 and microphone 418 are attached to brace 410 using a C-shaped holder 428. In one embodiment, holder 428 has a horizontal extension rod (not visible in FIG. 4) at the proximal end of the C. The extension rod fits between the lips and positions the proximal end of the C just outside the mouth. The distal end of the C (labeled 426 in FIG. 4) is attached to a handle 424 that is connected to the backside of speaker 416. Operator 102 can use handle 424, e.g., to hold sensor assembly 400 when brace 410 is being inserted into and secured inside the mouth. An electrical cable 422 for providing electrical connections to speaker 416 and microphone 418 is fitted through handle 424 as indicated in FIG. 4. Depending on the length of holder 428 and the point of attachment of distal end 426 to handle 424, speaker 416 and microphone 418 can be placed (1) outside of the operator's mouth, (2) inside the operator's mouth, or (3) between the operator's lips. In the second and third configurations, operator 102 needs to keep his/her mouth slightly open to enable sensor assembly 400 to probe vocal tract 102. In the first configuration, the mouth can be closed, and speaker 416 and microphone 418 can be used for tracking the lips. Similar to the tongue movements that can be detected using sensor assemblies 200 and 300 (see FIGS. 2-3), lip movements detected using sensor assembly 400 can be used to generate control signal 138 for controller 140 (FIG. 1).

In one embodiment, microphone 418 and speaker 416 are mounted in an axially symmetric configuration, with the microphone placed in front of the speaker using a crossbeam 420 whose ends are attached to the outer rim of the speaker as indicated in FIG. 4. The diameter of microphone 418 is smaller than the diameter of the active area of speaker 416, which enables the acoustic waves generated by the speaker to go around the microphone toward the mouth and/or vocal tract of operator 102. The reflected acoustic waves are detected by microphone 418, and the resulting electrical signals are directed, via cable 422, to processor 124 (FIG. 1) for processing and analysis.

In an alternative embodiment, the diameter of microphone 418 does not have to be smaller than the diameter of the active area of speaker 416 and/or a different placement geometry of the microphone and speaker with respect to one another (e.g., side by side) can similarly be used.

Figure 5A:
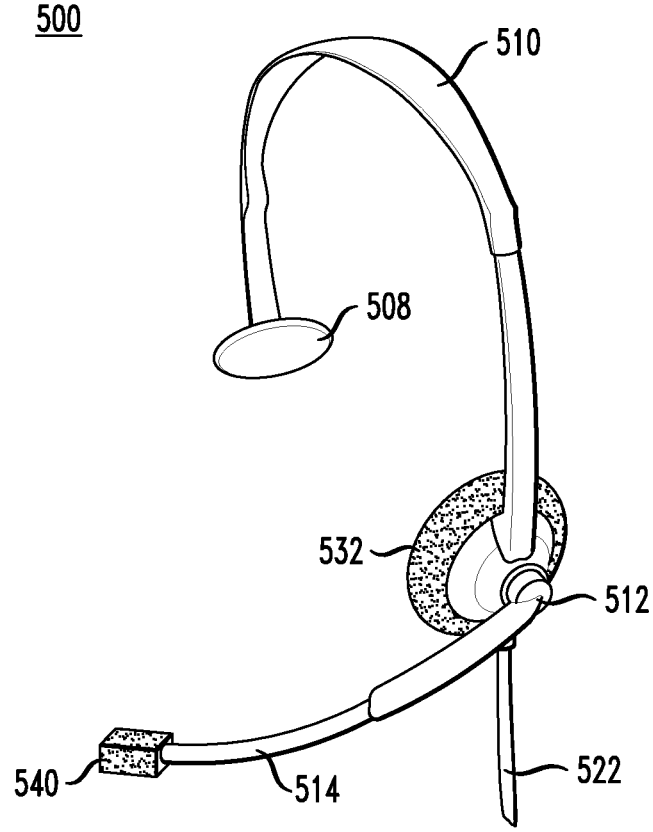
FIGS. 5A-5B show perspective three-dimensional views of a headset and its certain components that can be used in the HM interface of the system shown in FIG. 1 according to yet another embodiment of the invention.
Figure 5B:
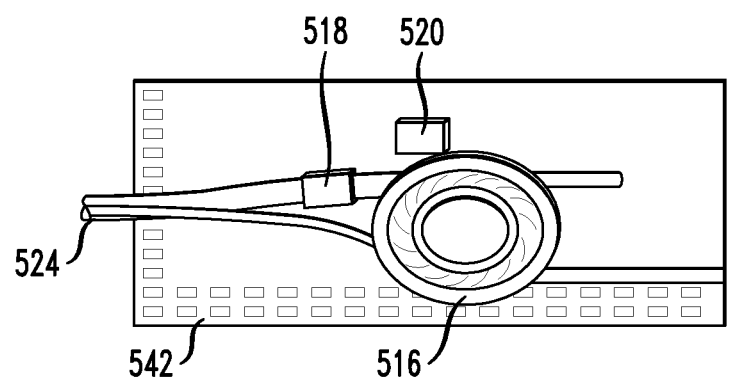

FIGS. 5A-5B show perspective three-dimensional views of a headset 500 that can be used in HM interface 110 (FIG. 1) according to yet another embodiment of the invention. More specifically, FIG. 5A shows an overall view of headset 500. FIG. 5B shows an enlarged view of a circuit 544 located in a sensor assembly 540 of headset 500.

Referring to FIG. 5A, headset comprises a headband 510 with a temple pad 508 attached at one end and an earcup 532 attached at the other end. Connected to earcup 532 is a boom arm 514 having sensor assembly 540 at its distal end. A ball joint 512 located between earcup 532 and boom arm 514 enables two degrees of freedom for rotating the boom arm with respect to the earcup. More specifically, a first degree of freedom corresponds to a rotation that moves the distal end of boom arm 514 approximately up or down. A second degree of freedom corresponds to a rotation that moves the distal end of boom arm 514 in (toward the lips) or out (away from the lips) in the horizontal plane. In one embodiment, earcup 532 and a speaker housed therein (not explicitly shown in FIG. 5A) implement earpiece 132 (FIG. 1). A cable 522 provides appropriate electrical connections for the circuitry housed in ear cup 532 and in sensor assembly 540.

Referring to FIG. 5B, circuit 544 includes a speaker 516, a MEMS microphone 518, and a miniature video camera 520, all mounted on a circuit board 542. An extension 524 of cable 522 provides electrical connections for circuit board 542 and the various circuit elements connected thereto. Speaker 516 and microphone 518 can be used to track the motion of the lips of operator 102, e.g., as already described above in reference to FIG. 4. Images captured by video camera 520 can be used by HM interface 110 to determine the position of sensor assembly 540 with respect to certain reference points, such as the maxillary anterior teeth in the mouth of operator 102. The determined sensor position is taken into account by processor 124 to make appropriate adjustments in the analysis of the acoustic echo signals detected by microphone 518.

In one embodiment, video camera 520 is a CameraCube manufactured by OmniVision Technologies, Inc., of Santa Clara, Calif.

While this invention has been described with reference to illustrative embodiments, this description is not intended to be construed in a limiting sense.

In various embodiments, HM interface 110 may have more than one biometric-sensor assembly. For example, headset 500 (FIG. 5) can be used together with sensor assembly 200 (FIG. 2) or sensor assembly 300 (FIG. 3).

Although sensor assemblies 200, 300, 400, and 540 (FIGS. 2-5) have been described in reference to HM interface 110, the use of said sensor assemblies is not so limited. Various embodiments of sensor assemblies 200, 300, 400, and 540 can similarly be used in other suitable systems. One representative example of such other system is a voice-estimation interface disclosed in the above-cited U.S. Patent Application Publication No. 2010/0131268. Another representative example is the use of sensor assembly 540 (FIG. 5) for lip-reading.

For the purposes of this specification and claims, the various articulators of vocal tract 104, such as the velum, tongue, lips, and jaws, are considered to be parts of the vocal tract.

In various embodiments, variously shaped dental appliances known in the dental arts can be adapted to implement mouthpieces (e.g., analogous to mouthpiece 210, FIG. 2) and/or dental braces (e.g., analogous to braces 310 and 410, FIGS. 3-4) without departing from the scope and principle of the invention(s).

Various wireless arrangements, such as inductively coupled loops, can be used to power circuits located in the mouth of operator 102.

As used in the claims, the term "machine" should be construed to cover, for example, any of (i) a device or system comprising fixed and/or moving parts that modifies or transfers energy and/or generates mechanical movement, (ii) an electronic device or system, e.g., a computer, a radio, a telephone, or a consumer appliance, (iii) an optical device or system, (iv) an acoustic device or system, (v) a vehicle, (vi) a weapon, (vii) a piece of equipment that performs or assists in the performance of a human task, and (viii) a semi or fully automated device that magnifies human physical and/or mental capabilities in performing one or more operations.

Various modifications of the described embodiments, as well as other embodiments of the invention, which are apparent to persons skilled in the art to which the invention pertains are deemed to lie within the principle and scope of the invention as expressed in the following claims.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

The description and drawings merely illustrate the principles of the invention. It will thus be appreciated that those of ordinary skill in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The functions of the various elements shown in the figures, including any functional blocks labeled as "processors," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

What is claimed is:

1. An apparatus, comprising:
a first acoustic speaker;
a first set of one or more first acoustic microphones; and
a dental appliance, wherein:
the first acoustic speaker and the first set of one or more first acoustic microphones are attached to the dental appliance so that, when the dental appliance is placed into a user's mouth:
the first acoustic speaker has a position that causes acoustic waves generated by the first acoustic speaker to enter the user's vocal tract; and
the first set of one or more first acoustic microphones has a position that causes acoustic waves reflected from the vocal tract to impinge onto at least one of the first acoustic microphones;
a second acoustic speaker configured to generate second acoustic waves;
a second acoustic microphone; and
a headset having an earpiece and a boom arm that is movable with respect to the earpiece, wherein both the second acoustic speaker and the second acoustic microphone are mounted on the boom arm, wherein:
when the headset is placed onto the user's head, the boom arm is configurable for:
the second acoustic speaker to have a position that causes the second acoustic waves to reflect off the user's lips; and
the second acoustic microphone to have a position that causes reflected second acoustic waves to impinge onto the second acoustic microphone.

2. The apparatus of claim 1, wherein the dental appliance comprises a mouthpiece having a first groove and a second groove located on opposite sides of the mouthpiece and configured to accommodate an upper arch of teeth and a lower arch of teeth, respectively, when inserted into the mouth.

3. The apparatus of claim 2, wherein the first and second grooves are configured to lock the user's mandible and maxilla with respect to one another.

4. The apparatus of claim 2, wherein:
the first acoustic speaker is imbedded into a lingual wall of the mouthpiece; and
the first set of one or more first acoustic microphones is imbedded into the lingual wall.

5. The apparatus of claim 2, further comprising a set of electrical wires configured to provide electrical connections to the first acoustic speaker and/or the first set of one or more first acoustic microphones, wherein the electrical wires protrude out from a labial wall of the mouthpiece.

6. The apparatus of claim 2, wherein:
the mouthpiece has a U shape characterized by an approximate-symmetry plane;
at least one microphone of the first set is located to one side of the approximate-symmetry plane; and
at least one other microphone of the first set is located to another side of the approximate-symmetry plane.

7. The apparatus of claim 1, wherein:
the dental appliance comprises a dental brace shaped to form-fit a specified arch of teeth;
the first acoustic speaker is attached to the dental brace; and
the first set of one or more first acoustic microphones is attached to the dental brace.

8. The apparatus of claim 7, wherein the specified arch is a lower arch.

9. The apparatus of claim 7, wherein the first acoustic speaker is attached to the dental brace so that, when the dental brace is placed in the mouth, the first acoustic speaker is located inside the mouth.

10. The apparatus of claim 7, wherein the first set of one or more first acoustic microphones is attached to the dental brace so that, when the dental brace is placed in the mouth, the first set of one or more first acoustic microphones is located inside the mouth.

11. The apparatus of claim 7, wherein the first acoustic speaker is attached to the dental brace so that, when the dental brace is placed in the mouth, the first acoustic speaker is located between the user's lips.

12. The apparatus of claim 1, further comprising a video camera mounted on the boom arm.

13. The apparatus of claim 1, further comprising a power source configured to provide electrical power to the first acoustic speaker and/or the first set of one or more first acoustic microphones, wherein the power source is incorporated into or attached to the dental appliance.

14. The apparatus of claim 1, further comprising a wireless transceiver configured to:
receive control signals for the first acoustic speaker from an external transmitter; and/or
transmit signals generated by the first set of one or more first acoustic microphones to an external receiver, wherein the wireless transmitter is incorporated into or attached to the dental appliance.

15. An apparatus, comprising:
a first acoustic speaker;
a first set of one or more first acoustic microphones;
a second acoustic speaker;
a second acoustic microphone; and
a dental appliance, wherein:
the first acoustic speaker, the first set of one or more first acoustic microphones, the second acoustic speaker, and the second acoustic microphone are attached to the dental appliance so that, when the dental appliance is placed into a user's mouth:
the first acoustic speaker has a position inside the user's mouth that causes acoustic waves generated by the first acoustic speaker to enter the user's vocal tract;
the first set of one or more first acoustic microphones has a position inside the user's mouth that causes acoustic waves reflected from the vocal tract to impinge onto at least one of the first microphones;
the second acoustic speaker is configured to generate second acoustic waves and has a position outside the user's mouth that causes the second acoustic waves to reflect off the user's lips; and the second acoustic microphone has a position outside the user's mouth that causes reflected second acoustic waves to impinge onto the second acoustic microphone.

16. The apparatus of claim 15, wherein:

the dental appliance comprises a dental brace shaped to form-fit a specified arch of teeth;

the first acoustic speaker is attached directly to the dental brace; and the first set of one or more acoustic microphones is attached directly to the dental brace; and the second acoustic speaker and the second acoustic microphone are attached to a distal end of a holder, wherein a proximal end of the holder is attached to the dental brace so that a part of the holder is configured to fit between the user's lips.

* * * * *